United States Patent [19]

Sasagawa et al.

[11] Patent Number: 4,951,135
[45] Date of Patent: Aug. 21, 1990

[54] ELECTRONIC-TYPE ENDOSCOPE SYSTEM HAVING CAPABILITY OF SETTING AGC VARIATION REGION

[75] Inventors: Katsuyoshi Sasagawa; Masahiko Sasaki; Masao Uehara; Katsuyuki Saito, all of Hachioji; Jun Hasegawa, Hino; Masahide Kanno, Hachioji; Akinobu Uchikubo, Hachioji; Shinji Yamashita, Hachioji, all of Japan

[73] Assignee: Olympus Optical Co., Ltd., Tokyo, Japan

[21] Appl. No.: 290,943

[22] Filed: Dec. 28, 1988

[30] Foreign Application Priority Data

Jan. 11, 1988 [JP] Japan .................. 63-277794
Feb. 26, 1988 [JP] Japan .................. 63-44706

[51] Int. Cl.$^5$ .................. A61B 1/04; A61B 1/06; H04N 5/20
[52] U.S. Cl. .................. 358/98; 128/6; 358/168
[58] Field of Search .................. 358/98, 93, 168; 128/6, 128/4, 5

[56] References Cited

U.S. PATENT DOCUMENTS

| | | | |
|---|---|---|---|
| 4,532,918 | 8/1985 | Wheeler | 358/168 |
| 4,535,758 | 8/1985 | Longacre, Jr. | 358/98 |
| 4,628,362 | 12/1986 | Waehner | 358/168 |
| 4,631,582 | 12/1986 | Nagasaki et al. | 358/98 |
| 4,821,116 | 4/1989 | Nagasaki et al. | 358/98 |
| 4,839,723 | 6/1989 | Yoshinaga et al. | 358/98 |
| 4,853,773 | 8/1989 | Hibino et al. | 358/98 |
| 4,855,819 | 8/1989 | Hibino et al. | 128/6 |
| 4,860,094 | 8/1989 | Hibino et al. | 358/93 |

FOREIGN PATENT DOCUMENTS

3808011A1 9/1988 Fed. Rep. of Germany ........ 358/98
62-211040 9/1987 Japan .

Primary Examiner—Howard W. Britton
Assistant Examiner—Tommy D. Lee
Attorney, Agent, or Firm—Armstrong, Nikaido, Marmelstein, Kubovcik & Murray

[57] ABSTRACT

An endoscope system has a signal processing circuit for converting an image signal output of a solid state imaging device into a standard image signal, a monitor for providing a display of the standard image signal, an automatic gain control circuit for outputting an image signal whose level is automatically adjusted in accordance with the level of the image signal; and a gain variation region setting circuit for outputting a control signal to set the gain variation region of the automatic gain control circuit. With this arrangement, it is possible to properly set the AGC variation region of the AGC of the signal processing apparatus in accordance with such factors as the number of pixels of the solid state imaging device which constitutes a part of an electronic endoscope connected.

23 Claims, 10 Drawing Sheets

|   | 1 | 2 | 3 | 4 | 5 | 6 | 7 |   |
|---|---|---|---|---|---|---|---|---|
| 1 | G | Mg | G | Mg | G | Mg | G | FIRST FIELD |
| 2 | Ye | Cy | Ye | Cy | Ye | Cy | Ye |  |
| 3 | G | Mg | G | Mg | G | Mg | G |  |
| 4 | Ye | Cy | Ye | Cy | Ye | Cy | Ye |  |
| 5 | G | Mg | G | Mg | G | Mg | G |  |
| ⋮ | Ye | Cy | Ye | Cy | Ye | Cy | Ye |  |
| ⋮ | G | Mg | G | Mg | G | Mg | G |  |

SECOND FIELD

ELECTRONIC-TYPE ENDOSCOPE SYSTEM HAVING CAPABILITY OF SETTING AGC VARIATION REGION

BACKGROUND OF THE INVENTION

1. Field of the Invention

The present invention relates to an electronic-type endoscope system provided with a changeover means for effecting changeover of the gain variation region of an automatic gain control means in accordance with the kind of electronic endoscope employed.

2. Description of the Related Art

In recent years, electronic-type endoscope systems having imaging means constituted by a solid state imaging device such as a charge-coupled device (hereinafter referred to as the "CCD") have been widely used. Such electronic-type endoscope systems fall into two major types: the type which employs an electronic endoscope (or electronic scope) whose front end portion includes such an imaging means and the type which employs an optical endoscope whose eyepiece portion is externally provided with a television camera including such an imaging means.

In such an electronic-type endoscope system having the imaging means for effecting photoelectric conversion, it is possible to easily implement signal processing of the output signals of the imaging means or to record them on a VTR or image file apparatus.

The current trend in the field of electronic-scope applications is to appropriately apply electronic scopes of various types, from a small-diameter type to a large-diameter type, to different portions to be observed. Accordingly, it has been proposed to use various kinds of built-in solid state imaging devices in accordance with the outer diameters of the inserting sections of electronic scope employed.

Where an electronic-type endoscope system employing one signal processing system is combined with an electronic scope employing an imaging means consisting of a plurality of solid state imaging devices, it is necessary to establish the system's environment in accordance with the kind of solid state imaging device.

Japanese Patent Laid-open No. 211040/1987 discloses an example of a prior art arrangement in which the requisite function can be selected in accordance with the kind of endoscope connected.

In the above-described prior art arrangement, initialization as to the execution or non-execution of image reversal, the presence or absence of a mask configuration, and so on, is carried out in accordance with the kind of endoscope connected. However, it has been impossible to combine the prior art arrangement with imaging means of various types each employing a solid state imaging device consisting of a different number of pixels.

Different types of optical systems are used in electronic scopes which employ imaging means consisting of solid state imaging devices having different numbers of pixels. In general, since such an electronic scope has a fixed focus, it is necessary to increase the f-number of the optical system disposed in front of the light receiving surface of the solid state imaging means in order to obtain a substantially focused image at a distance sufficiently long to allow observation. As the resolution of an image is enhanced, the f-number must be increased. If the f-number is increased, the quantity of light obtained at the light receiving surface of the solid state imaging device decreases even if the intensity of illumination of an object is kept constant. As a result, a deficiency of the quantity of light may easily occur. For this reason, an automatic gain control (hereinafter referred to as the "AGC") circuit is provided, and the AGC circuit serves to increase the gain of an image signal and set the level of the image signal to a proper level.

If a decrease in the quantity of light obtained at the light receiving surface of the solid state is compensated for by the above AGC circuit, particularly if the f-number is increased (for the case of high resolution), severe noise tends to occur.

Since the signals of high-resolution images contain high-frequency components, severe high-band noise tends to appear.

If the gain variation region of the AGC circuit is fixed, the use of an electronic scope whose resolution is not too high will enable an image to be displayed at a low noise level. However, for the above-described reason, if a high-resolution electronic endoscope is employed, an image containing severe noise may be reproduced and consequently the result of endoscopic inspection may be adversely affected. In addition, since the noise level differs, an operator may be afraid that his endoscope is an imperfect product.

SUMMARY OF THE INVENTION

It is, therefore, an object of the present invention to provide an electronic-type endoscope system which is capable of providing a high-quality image free of severe noise even if solid state imaging devices each having a different number of pixels are used.

It is another object of the present invention to provide an electronic-type endoscope system which is capable of providing an endoscopic image suitable for use with diagnosis.

Figure 1:
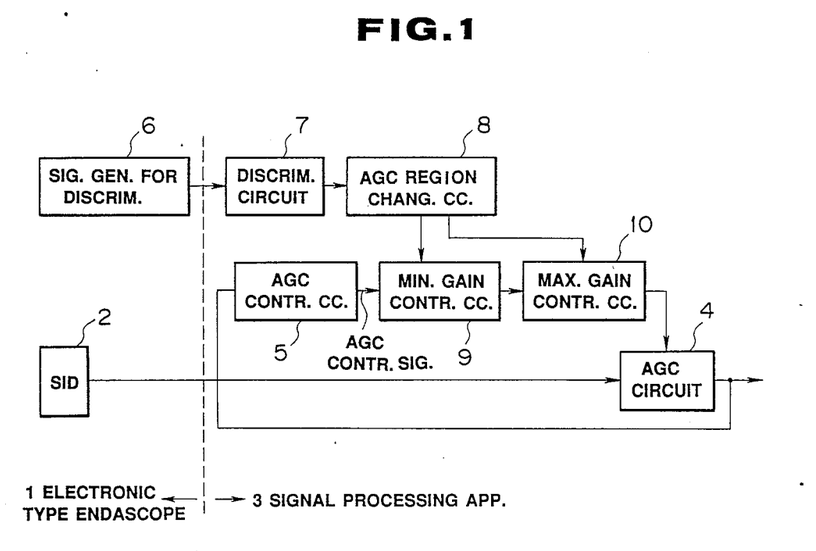
FIG. 1 is a conceptual diagram showing the construction of the essential portion of the present invention.

In the conceptual diagram shown in FIG. 1, the image signal which has been obtained by photoelectric conversion in a solid state imaging device (hereinafter referred to as the "SID") 2 of an electronic-type endoscope 1 is input to an AGC circuit 4 provided in a signal processing apparatus 3. The input signal is amplified by the AGC circuit 4, and one part of the output signal of the AGC circuit 4 is supplied to a signal processing system provided at the next stage, while the remaining part is input to an AGC control circuit 5. The AGC circuit 5 generates AGC control signals which serve to control the gain of the AGC circuit 4 so that the level of the image signal may become equal to a predetermined level (AGC reference level).

A discriminating-signal generating circuit 6 provided in the electronic-type endoscope 1 supplies a discriminating signal to the discriminating circuit 7, and the kind of discriminating signal, that is, the kind of electronic-type endoscope 1 is identified. The signal representing the result of the discrimination in the discriminating circuit 7 is input to an AGC region changeover circuit 8. In response to the output of the discriminating circuit 7, the AGC region changeover circuit 8 transmits control signals to a minimum-gain control circuit 9 and a maximum-gain control circuit 10, respectively. The minimum-gain control circuit 9 and the maximum-gain control circuit 10 set the minimum level and the maximum level of the AGC control voltage output from the AGC control circuit 5, respectively, in accordance with the above identified kind of electronic-type endoscope 1. Thus, the AGC variation region is set in accordance with the kind of electronic-type endoscope 1.

For example, where the gain of the AGC circuit 4 increases as the voltage of the AGC control signal rises, the minimum-gain control circuit 9 serves as a limiter whose output is kept at a level higher than a voltage Vmin corresponding to the minimum gain of the minimum-gain control circuit 9 even when the AGC control voltage falls below the voltage Vmin. Similarly, the maximum-gain control circuit 10 serves as a limiter which keeps the AGC control voltage at a level lower than a voltage Vmax corresponding to the maximum gain. Thus, the gain variation region of the AGC which matches the identified kind of electronic-type endoscope 1 is set, thereby making it possible to provide a display of a high-quality image.

DESCRIPTION OF THE PREFERRED EMBODIMENTS

Figure 2:
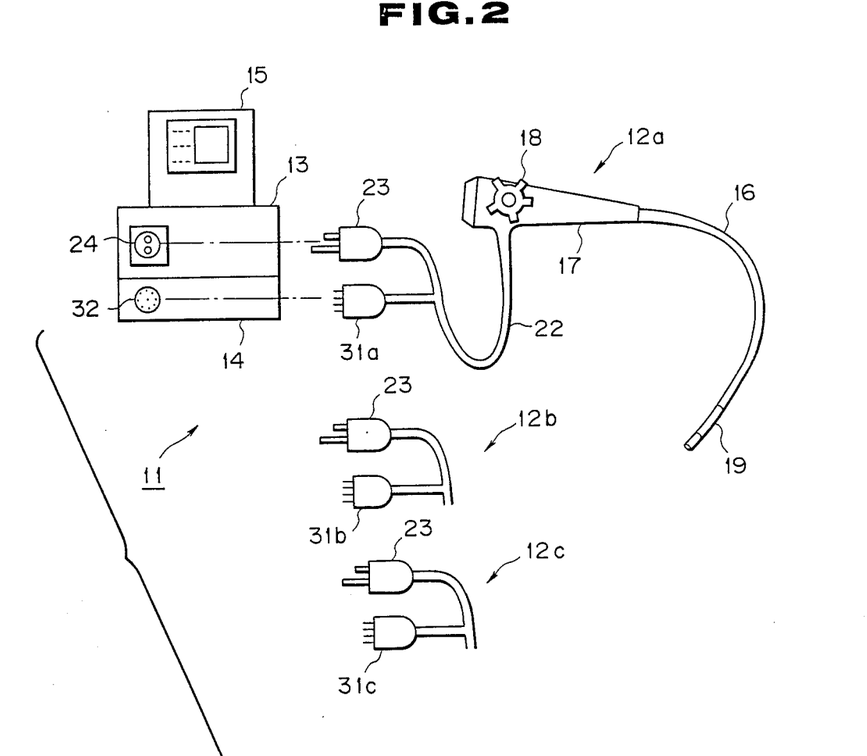
FIG. 2 is a diagrammatic view of the overall construction of an electronic-type endoscope system according to a first embodiment of the present invention.

As shown in FIG. 2, an electronic-type endoscope system 11 is constituted by three electronic endoscopes 12a, 12b and 12c (since the external configurations of the elements 12a, 12b and 12c are the same, the elements 12b and 12c are represented by their respective connector portions), a light source apparatus 13 for supplying illuminating light to each electronic endoscope 12i ($i=a, b, c$), a signal processing apparatus 14 for effecting signal processing of each of the electronic endoscopes 12i, and a color monitor 15 for providing a color display of the image signal output from the signal processing apparatus 14.

Each of the above electronic endoscopes 12i has an inserting section 16 which is formed in an elongated shape so that it can be inserted into a cavity of the human body, with an enlarged operating section 17 formed at the rear end of the inserting section 16. By rotating an angle knob 18 provided on the operating section 17, a flexible section 19 formed near the front end of the inserting section 16 can be freely curved in any direction.

Figure 3:
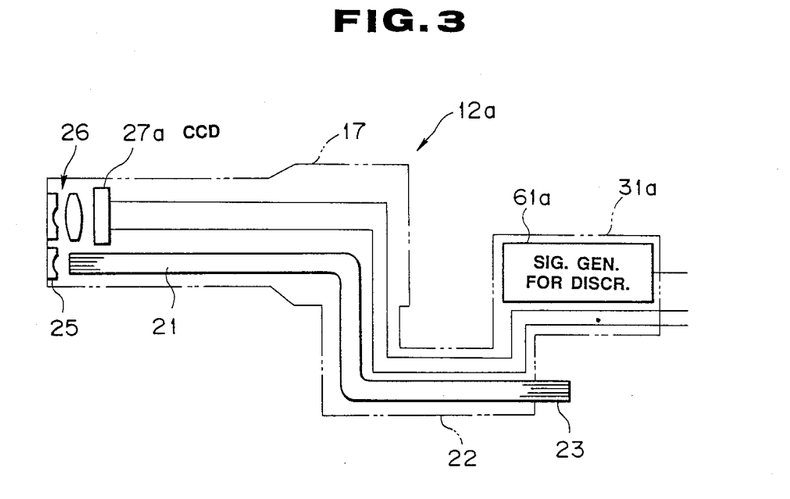
FIG. 3 is a diagrammatic view of the construction of the electronic-type endoscope according to the first embodiment.

As shown in FIG. 3, a light guide 21 is inserted through the inserting section 16, and the light guide 21 is further inserted through a light guide cable 22 which extends out of the inserting section 17. A light source connector 23 is attached to the extending end of the light guide cable 22 so that it can be connected to a connector receptacle 24 of the light source apparatus 13. By connecting the light source connector 23 to the light source connector receptacle 24, illuminating light is supplied to the entrance end surface of the light guide 21, transmitted to the exit end surface of the light guide 21, diverged by a projection lens 25, and projected onto an object.

Figure 4:
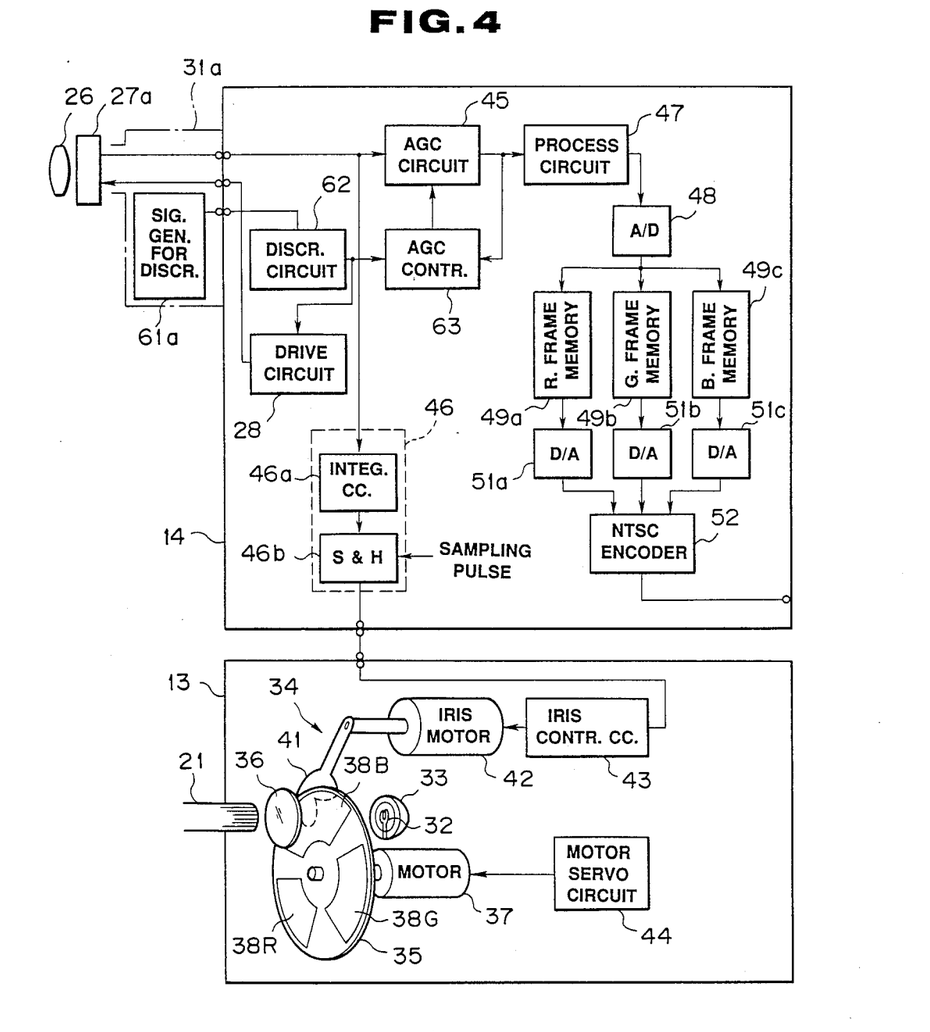
FIG. 4 is a block diagram of the constructions of both the signal processing apparatus and the light source apparatus which are used in the first embodiment.

An image of the object which is illuminated by the illuminating light passed through the projection lens 25 is incident upon an objective lens 26 which is attached to the front end of the inserting section 16, then focused on a CCD 27i (corresponding to each of the electronic endoscopes 12i) disposed in the focal plane of the objective lens 26. The thus-focused image is photoelectrically converted by the CCD 27i. Thus, as shown in FIG. 4, the photoelectrically converted image signal is read from the CCD 27i by the application of the CCD drive signals output from a CCD drive circuit 28 in the signal processing circuit 14. The CCD drive signals and the image signal are transferred over a signal cable to the signal processing apparatus 14. A signal connector 31i provided at one end of the signal cable can be connected to a connector receptacle 32 provided on the signal processing apparatus 14.

As shown in FIG. 4, the light source device 13 has a lamp 32 for generating white light, a convex mirror 33 for emitting the white light of the lamp 32 in the form of a beam of parallel rays, an iris device 34 for varying the quantity of light passed therethrough, a rotary color filter device 35 for decomposing the illuminating light controlled by the iris device 34 into the three primary colors: red, green and blue, and a condenser lens 36 for converging each of the three primary color onto the entrance end surface of the light guide 21.

The rotary color filter device 35 includes a rotary disk which is rotated by a motor 37, with three sector-shaped apertures formed in the rotary disk. Color transmission filters 38R, 38G and 38B, which respectively transmit light of wavelengths of red, green and blue are mounted in the respective apertures. The portions between the apertures for the color transmission filters 38R, 38G and 38B are formed as light shielding portions. The color transmission filters 38R, 38G and 38B are sequentially inserted into an optical path, and thus the object is illuminated by red, green and blue light in a frame-sequential manner and imaged by the CCD 27i by the illumination with each color light. Thus, when the CCD drive signal is applied to the CCD 27i during the period in which the illuminating light is occluded by the light shielding member, the image signal which has been photoelectrically converted and accumulated in the form of electrical charge is read from the CCD 27i. In consequence, the image signal which has been obtained by imaging under illumination with each color light is subjected to signal processing, so that frame sequential type color imaging is performed.

The iris device 34 is constituted by an iris blade 41 having a slit and an iris motor 42 to which the proximal end of the iris blade 41 is attached and which causes the iris blade 41 to rotate in the direction perpendicular to the optical axis so as to reduce the quantity of light passing through the optical axis. The rotary motion of the iris motor 42 is controlled by the driving signal supplied from an iris control circuit 43, and the quantity of light is controlled by changing the amount of rotation (the angle of rotation) of the iris motor 42.

The motor 37 which rotates the rotary color filter device 35 is controlled by a motor servo circuit 44 so that the speed of rotation of the motor 37 is kept constant.

The image signal which is read from the CCD 27i by the application of the above CCD drive signal is subjected to the elimination of a carrier and other predetermined processing in a pre-process circuit (not shown). Then, the thus-processed image signal is supplied to both an AGC circuit 45 and a light-adjustment-signal generating circuit 46 for generating a light adjustment signal. The output signal of the AGC circuit 45 is input to a process circuit 47, in which processes such as white balance and knee are implemented. Subsequently, the signal is input to an A/D converter 48, in which it is converted into a digital signal. The digital signal is supplied to any one of R, G and B frame memories 49a, 49b and 49c which correspond to the respective color fields, and thus image data for one image (one frame) is stored in R, G and B frame memories 49a, 49b and 49c in a sequential manner. For example, the image signal obtained by imaging under red illuminating light is stored in the R frame memory 49a. Subsequently, the image data stored in the R, G and B frame memories 49a, 49b and 49c is simultaneously read into corresponding D/A converters 51a, 51b and 51c, where the R, G and B image data is converted into corresponding analog color signals. The respective analog color signals are supplied to an NTSC encoder 52, converted into a composite video signal of the NTSC system, and supplied to a monitor.

The light-adjustment-signal generating circuit 46 outputs a light adjustment signal to an iris control circuit 43 so as to determine a proper image signal level in accordance with an input signal level, thereby controlling the amount of light adjustment. The light-adjustment-signal generating circuit 46 is constituted by, for example, an integrating circuit 46a and a sample and hold circuit 46b for holding the integrated output signal of the integrating circuit 46a for a period equivalent to one frame of a color image. The sample and hold circuit 46b outputs a light adjustment signal whose output level increases as the image signal level becomes large.

If use conditions vary, for example, from imaging of an object at a short distance to that of an object at a relatively long distance, the quantity of illuminating light is controlled in accordance with the light adjustment signal, whereby a proper intensity of illumination is automatically selected so that an image which enables an operator to easily make proper diagnosis or inspection can be obtained.

Figure 5:
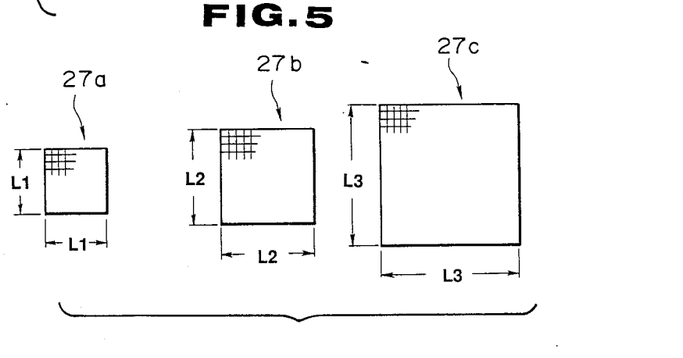
FIG. 5 serves to illustrate that imaging means having a different number of pixels can be used in the first embodiment.

In the first embodiment, the three electronic endoscopes 12a, 12b and 12c can be used. The respective electronic endoscopes 12a, 12b and 12c, as shown in FIG. 5, include imaging means constituted by CCDs 27a, 27b and 27 each having a different number of pixels. More specifically, the imaging means which employs the CCD 27a (whose size is, for example, L1×L1) including the smallest number of pixels (for example, twenty thousand pixels) is incorporated into the electronic endoscope 12a having a small-diameter inserting section. The imaging means which employs the CCD 27b (whose size is, for example, L2×L2) including the medium number of pixels (for example, fifty thousand pixels) is incorporated into the electronic endoscope 12b having a medium-diameter inserting section. The imaging means which employs the CCD 27c (whose size is, for example, L3×L3) including the largest number of pixels (for example, one hundred thousand pixels) is incorporated into the electronic endoscope 12c having a large-diameter inserting section.

For example, the electronic endoscope 22a having the smallest number of pixels can be inserted into the bronchial tubes, while the electronic endoscope 22c having the largest number of pixels can be used in a portion, such as the lower alimentary canal, which may accommodate an inserting section having a relatively large diameter, and, in addition, the endoscope 22c can provide an high-resolution image.

The signal connectors 31a, 31b and 31c of the respective electronic endoscopes 12a, 12b and 12c can be connected to the connector receptacle 32 of the signal processing apparatus 14, whereby it is possible to implement appropriate signal processing by discriminating among the electronic endoscopes 12a, 12b and 12c.

To this end, the signal connector 31i (31a in FIG. 4) of each electronic endoscope 12i is provided with a discriminating-signal generating circuit 61i, while a discriminating circuit 62 is provided in the signal processing apparatus 14. The discriminating signal generated by the discriminating-signal generating circuit 61i is identified by the discriminating circuit 62. A signal representing the result of the discrimination is input to an AGC control section 63. The AGC control section 63 sets the AGC variation region of an AGC circuit 45 to a value which matches the thus-identified electronic endoscope 12i. It is to be noted that the discriminating circuit 62 transmits the output signal to a drive circuit 28 to cause the drive circuit 28 to output a drive signal corresponding to the identified number of pixels. (For example, clock frequencies for horizontal and vertical transfers are set to values equivalent to the number of pixels in a horizontal line and that of pixels in a vertical line, respectively.)

Figures 6, 7:
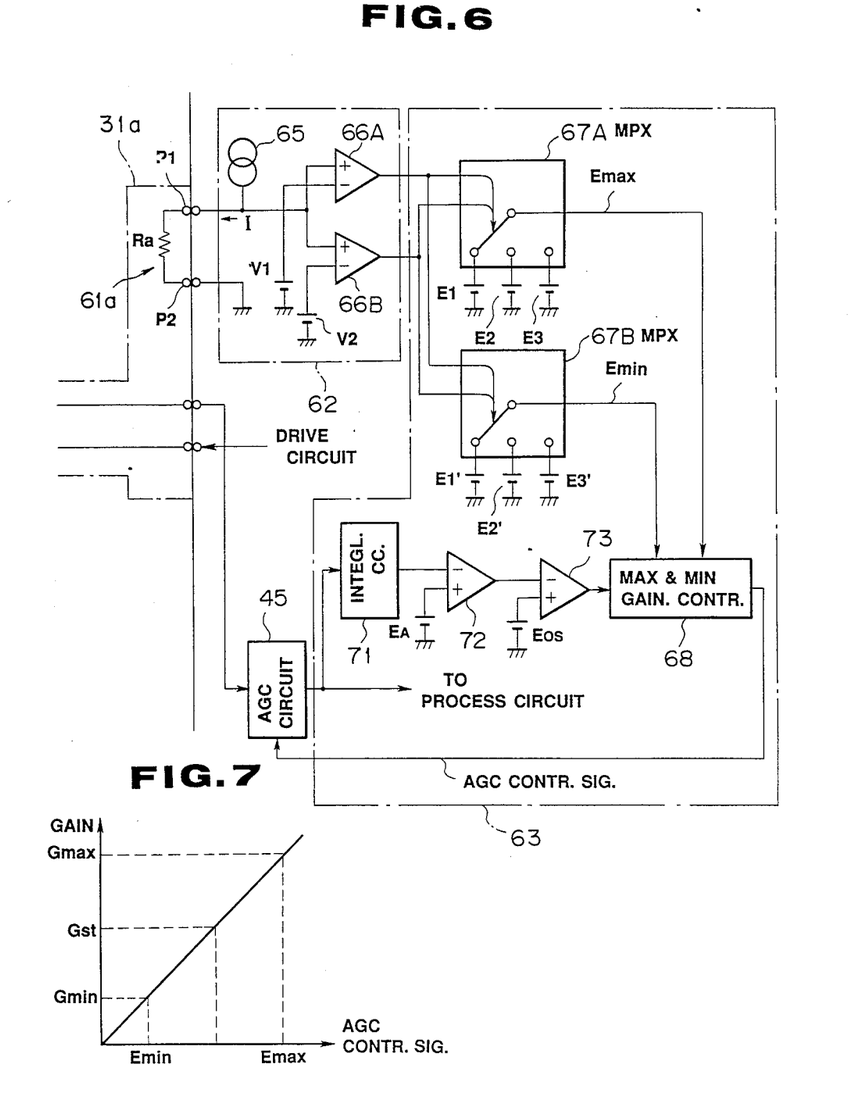
FIG. 6 is a circuit diagram showing the construction of an AGC control section which serves to set the gain variation region of the AGC circuit used in the first embodiment.
FIG. 7 is a characteristic chart showing the relationship between the gain of the AGC control circuit and the control voltage applied thereto in the first embodiment.

FIG. 6 shows the discriminating-signal generating circuit 61a, the discriminating circuit 62 and the AGC control circuit 63, respectively.

The discriminating-signal generating circuit 61a includes a discriminating resistor Ra which is connected to, for example, two connector pins P1 and P2. In the discriminating circuit 62 of the signal processing apparatus 14, pin receptacles which are connected to the connector pins P1 and P2 are connected to the output terminal of a constant current source 65 and ground, respectively. A constant current I, which is output from the constant current source 65, flows through the resistor Ra. The resulting voltage RaI of the resistor Ra is applied to, for example, one input terminal of each comparator 66A and 66B. The voltages RaI thus applied are compared with corresponding constant voltages V1 and V2 applied to the other input terminals of the respective comparators 66A and 66B. The levels of the constant voltages V1 and V2 are selected so that, for example, the relationship of V1>V2 is established. The value of a resistor Ri (i=a, b, c) which is disposed in correspondence with the CCD 27i is selected so that, for example, V1, V2>RaI, V1>RbI>V2, RcI>V1, V2 may be obtained. Accordingly, it is possible to discriminate among the three CCDs 27i by using the outputs of the two comparators 66A and 66B. In this case, the two comparators 66A and 66B respectively output "L" and "L", "L" and "H" as well as "H" and "H" in accordance with the values of the respective resistors Ra, Rb and Rc. The output signals of the respective comparators 66A and 66B are applied to the address terminals of the respective analog multiplexers 67A and 67B. Each of the analog multiplexers 67A and 67B has three input terminals to which voltages E1, E2, E3 or E1', E2', E3' are applied. The analog multiplexer 67A selectively outputs the voltage E1, E2 or E3 from its output terminal in the address specified by the output of the comparator 66A, while the analog multiplexer 67B selectively outputs the voltage E1', E2' or E3' from its output terminal in the address specified by the output of the comparator 66B. In this case, any one of the voltages E1, E2 and E3 takes on the maximum voltage value of the AGC control voltage, while any one of the voltages E1', E2' and E3' takes on the minimum voltage value of the AGC control voltage. For example, in the case of the CCD 27a (, that is, where the outputs of the comparators 66A and 66B are "L" and "L", respectively), the multiplexers 67A and 67B output E1 and E1', respectively. Simultaneously, in the case of the CCD 27b, the multiplexers 67A and 67B respectively output E2 and E2' and, in the case of the CCD 27c, E3 and E3'. That is to say, voltages Ej and Ej' (j=1, 2 or 3) which are combined in pair take on the maximum voltage Emax and the minimum voltage Emin, respectively, during AGC operation. The voltages Ej and Ej' which have been thus selected in the respective multiplexers 67A and 67B are input to a maximum/minimum gain control circuit 68.

Figure 8:
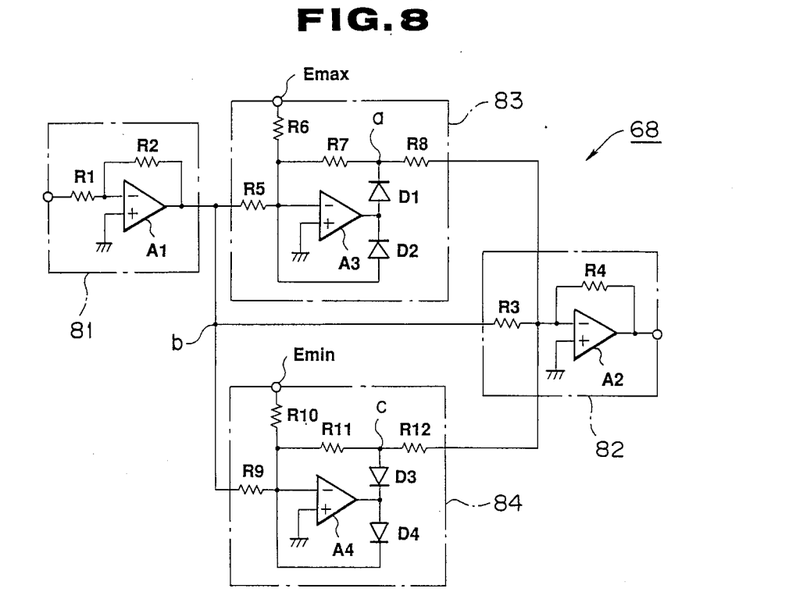
FIG. 8 is a circuit diagram of the maximum-gain control circuit and the minimum gain control circuit in the first embodiment.

As shown in FIG. 7, the AGC circuit 45 is a circuit whose gain increases as the magnitude of the AGC control signal increases. The output of the AGC circuit 45 is input to an integrating circuit 71, where it is envelope-detected (integrated) and converted into a signal having a level corresponding to the brightness of an object. The resultant signal is input to an error generating circuit 72, and the difference between the level of the signal and a predetermined level EA is output. More specifically, if the output of the integrating circuit 71 is lower than the level EA, a signal output in the positive direction is provided. If not, a signal in the negative direction is provided. The output of the error generating circuit 72 is input to an offset adding circuit 73. The offset adding circuit 73 adds an offset voltage Eos to the input signal and supplies the result to the maximum/minimum gain control circuit 68. The maximum/minimum gain control circuit 68 serves as a limiter circuit which limits voltages deviating from the region between voltages Ej' and Ej so that the level of the AGC control signal may be kept within the range from E1 to E1', E2 to E2' or E3 to E3'. FIG. 8 shows the construction of the maximum/minimum gain control circuit 68.

The input signal of the circuit 68 is inverted and amplified by a first inverting amplifier 81 which is constituted by resistors R1 and R2 as well as an operational amplifier (hereinafter referred to as the "OP" amplifier) A1. The output of the inverting amplifier 81 is input to a second inverting amplifier 82 which is constituted by resistors R3 and R4 as well as an OP amplifier A2, then inverted and amplified, and then output from the output terminal of the OP amplifier A2.

The output of the first inverting amplifier 81 is input to both a first limiter circuit 83 and a second limiter circuit 84. The outputs of the first and second limiter circuits 83 and 84 are input to a second inverting amplifier 82.

The first limiter circuit 83 is constituted by resistors R5, R6, R7 and R8, an OP amplifier A3 and diodes D1 and D2. The voltage Emax is applied via the resistor R6 to an OP amplifier A3. The first limiter circuit 83 is a circuit which prevents the output of a signal above Emax even if the level of an input signal becomes excessively high. More specifically, in the first limiter circuit 83 as long as the level of an input signal does not exceed Emax, no voltage is produced at a point a. This is because when the input level is not higher than Emax, the diode D1 is reverse-biased. When the input level becomes higher than Emax, the portion of the voltage which exceeds Emax is generated at the point a as a voltage of polarity opposite to that of the voltage at a point b. More specifically, when the level of the input signal exceeds the voltage Emax, the excess is cancelled and, therefore, the output level does not increase above Emax.

The second limiter circuit 84 is constituted by resistors R9, R10, R11, R12, an OP amplifier A4, and diodes D3 and D4. In the second limiter circuit 84, the voltage Emin is applied to the input terminal of the OP amplifier through the resistor R10. In this limiter circuit 84, when the level of its input level falls below the voltage Emin, the portion of the voltage which falls below Emin is generated at the point b as a voltage of polarity opposite to that of the voltage at the point b, and the portion of the voltage which falls below the voltage Emin is cancelled.

Figure 9:
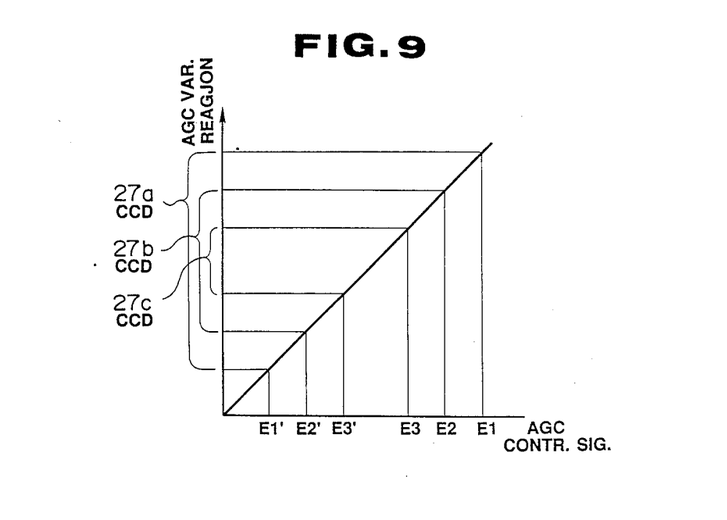
FIG. 9 is a graph which serves to illustrate one example of the AGC variation region which is set when three CCDs are used in the first embodiment.

In the first embodiment having the above-described arrangement, when the electronic endoscope 12i is connected to the signal processing apparatus 14, the number of pixels of the CCD 27i of the electronic endoscope 12i is detected, and the AGC variation region of the AGC circuit 45 is automatically set to a proper value in accordance with the number of pixels. For example, as shown in FIG. 9, in the case of the CCD 27a having the smallest number of pixels, the AGC variation region is set in the range from E1 to E1'; in the case of the CCD 27b having the medium number of pixels, the AGC variation region is set in the range from E2 to E2'; and, in the case of the CCD 27c having the largest number of pixels, the AGC variation region is set in the range from E3 to E3'. Where the AGC variation region deviates from any of the above ranges, for example, where the distance to an object is large and the resultant input signal level is small and therefore the AGC control voltage exceeds Emax, the AGC control voltage is held at a fixed value (that is, Emax). Accordingly, the AGC circuit 45 does not excessively increase the gain. It is, therefore, possible to prevent severe noise from appearing in an image during reproduction. In this case, since an image displayed is dark compared with proper brightness, an observer can understand that the use conditions are not proper and, therefore, imaging should be performed at a location even closer to the object.

Although FIG. 9 shows one example of the gain variation region which is set for each of the CCDs 27a, 27b and 27c, the setting is not limited only to that shown in FIG. 9.

Figure 10:
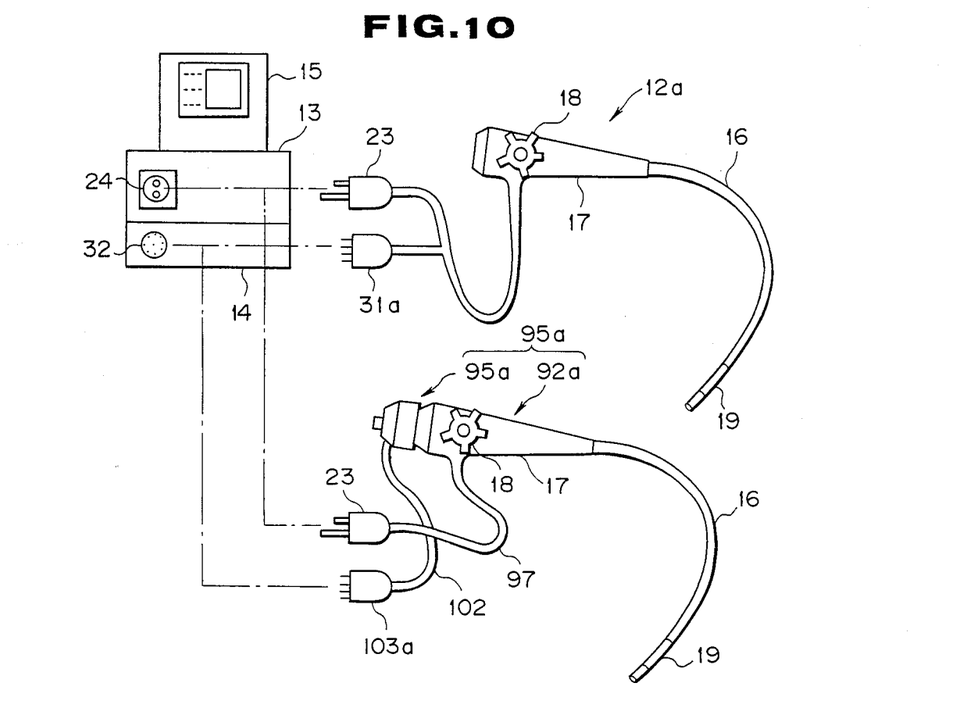
FIG. 10 is a block diagram of the overall construction of an electronic-type endoscope system according to a second embodiment of the present invention.
Figure 11:
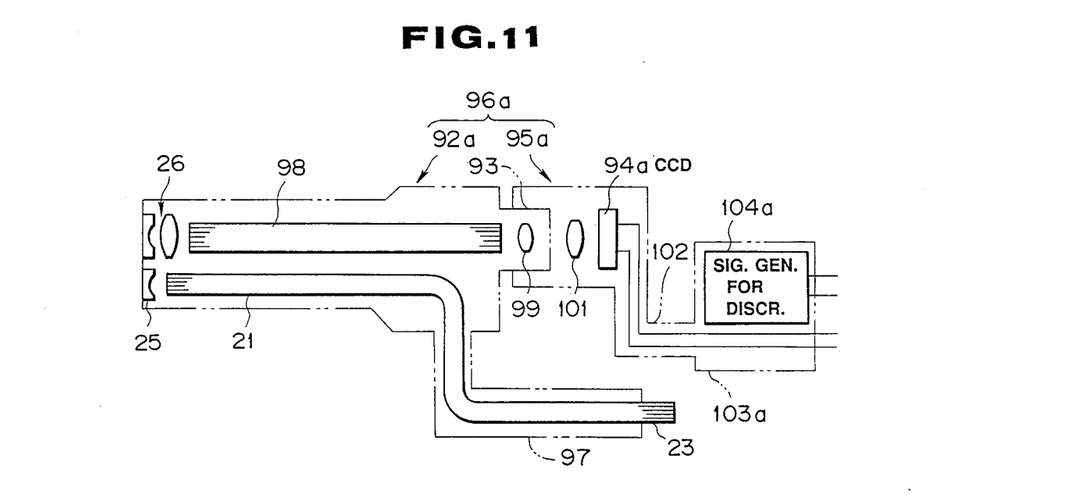
FIG. 11 is a schematic view showing the construction of a fiber scope which constitutes a part of the second embodiment and the construction of a television camera connected to the fiber scope.

FIGS. 10 and 11 show an electronic-type endoscope system according to a second embodiment of the present invention.

In the first embodiment, only the electronic endoscopes 12i are connected to the signal processing apparatus 14. In accordance with the second embodiment, it is possible to employ an electronic endoscope 96i in which, as shown in FIG. 11, a television camera 95i including a CCD 94i is attached to an eyepiece portion 93 of a fiber scope 92i such as an optical endoscope. (In FIG. 11 and 10, i is represented by a for the purpose of illustration only.)

The fiber scope 92a has an external configuration which is approximately similar to that of the electronic endoscope 12i. (The same reference numerals are used to denote the elements that are the same as those of the electronic endoscope 12i.) In the second embodiment, the eyepiece portion 93 is formed at the rear end of the operating section 17, and a light guide cable 97 extends from the operating section 17 and the light source connector 23 is provided at the extending end of the light guide cable 97 so that it can be connected to the connector receptacle 24.

As shown in FIG. 11, the fiber scope 92a is provided with an image guide 98 whose entrance end surface is located in the focal plane of the objective lens 26. An optical image transferred by the image guide 98 can be visually observed through an eyepiece lens 99 which is opposed to the exit end surface of the image guide 98. In addition, if the television camera 95a is connected to the eyepiece portion 93, the optical image is focused on the light receiving surface of the CCD 94a by a focusing lens 101.

A signal connector 103a, which is provided at the extending end of a signal cable 102 of the television camera 95a, can be connected to the signal connector receptacle 32, and the signal connector 103a includes a discriminating-signal generating circuit 104a. The discriminating-signal generating circuit 104a is constituted by, for example, a discriminating resistor such as that shown in FIG. 6.

In the first embodiment, the gain variation region of the AGC circuit 45 is selectively set in correspondence with the number of pixels of the CCD 21i used in the electronic endoscope 12i. In contrast, the second embodiment is arranged to identify the number of pixels of, for example, the CCD 27i and the number of pixels of the CCD 94i of the television camera 95i as well as a lens system constituting imaging means, that is, the objective lens 26 and the focusing lens 101. (Accordingly, the kind of signal generated by the discriminating-signal generating circuit is changed.) Thus, the gain variation region of the AGC circuit 45 can automatically be set to a range which matches each imaging means. Even if the number of pixels is the same, the proper value of the gain variation region may be automatically changed by taking into account the brightness of the focusing lens system.

The present invention is not limited to a frame sequential type color imaging means for effecting color imaging under illumination using frame-sequential light of red, green and blue, and is likewise applicable to an electronic type endoscope system using a built-in color-filter type imaging means for effecting color imaging under illumination using white light. The following is a description of the embodiment for carrying out the latter arrangement.

Figure 12:
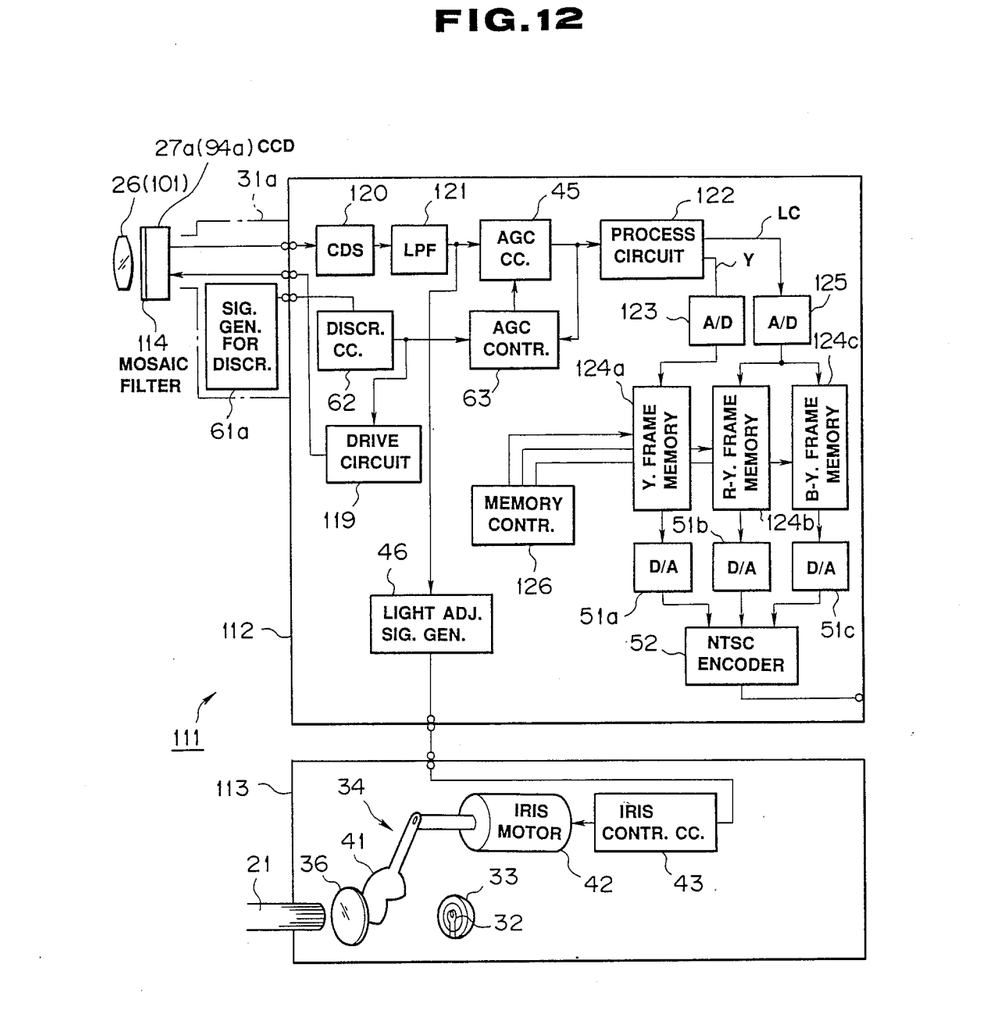
FIG. 12 is a block diagram showing the constructions of the signal processing apparatus and the light source apparatus used in the third embodiment of the present invention.

FIG. 12 shows the constructions of a signal processing apparatus 112 and a light source apparatus 113 in an electronic-type endoscope system 111 according to a third embodiment of the present invention.

The third embodiment is suitable for use with an imaging means in which a color mosaic filter 114 is attached to the front of the CCD 27i.

Figure 13A:
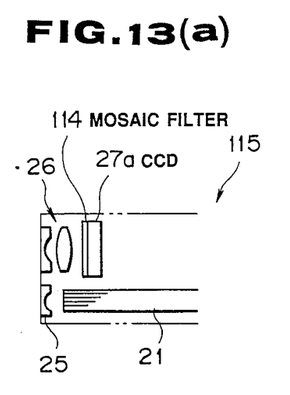
FIGS. 13a and 13b are schematic illustrations showing the portion of imaging means provided with a color filter device in the third embodiment.
Figure 13B:
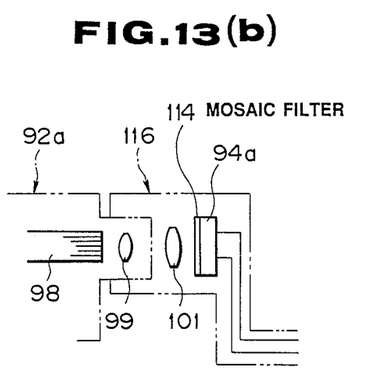

The imaging means may be an electronic endoscope or a television camera attached to the eyepiece portion of a fiber scope. For example, in the case of an electronic endoscope 115, it is possible to use an imaging means, shown in FIG. 13a, in which the color mosaic filter 114 is attached to the front of the CCD 27a shown in FIG. 13a. In the case of a television camera 116, it is possible to use an imaging means, shown in FIG. 13b, in which the color mosaic filter 114 is attached to the front of the CCD 94a of the television camera 116 shown in FIG. 13b. The remaining portion of the endoscope system provided with the imaging means of FIG. 13a is identical in construction to that of the endoscope system provided with the imaging means of FIG. 13b and, therefore, the same elements are represented by the same reference numerals (the essential portion alone is shown).

The light source apparatus 113 which constitutes a part of the endoscope system 111 has none of the color filter device 35, the motor 37, and the motor servo circuit 44 which are incorporated in the frame sequential-type light source apparatus 13 shown in FIG. 4, and the white light is made incident upon the entrance end surface of the light guide 21 through the iris blade 41 and the condenser lens 36.

The illuminating light is transferred by the light guide 21, passed from the front end surface of the light guide 21 through the projection lens 25, and projected toward an object. Light reflected from the illuminated object is incident upon the objective lens 26, which forms an optical image on its focal plane. In the case of the electronic endoscope 115, the CCD 27i to which the color mosaic filter 114 is attached is disposed in the focal plane, and color separation is implemented for each pixel by the color mosaic filter 114. In the case of the fiber scope 92i, light reflected from the illuminated object is incident upon the entrance end surface of the image guide 98, transferred by the image guide 98, passed through the eyepiece lens 99 and the focusing lens 101, and focused on the CCD 94i to which the color mosaic filter 114 is attached.

Figure 14:
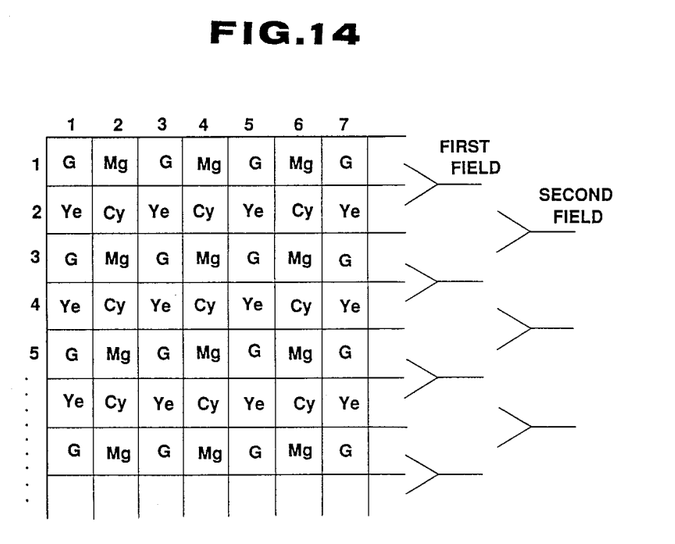
FIG. 14 is a view which serves to illustrate the arrangement of the constituent elements of the color filter device used in the third embodiment.

The color mosaic filter 114 which is attached to the front of the CCD 27i or the CCD 94i is a complimentary color-type color mosaic filter such as that shown in FIG. 14.

The CCD 27i or 94i to which the complimentary color-type color mosaic filter 114 is attached is, for example, an interline-type CCD in which light receiving portions (storage portions for storing charges obtained by photoelectric conversion) and transfer portions for transferring stored charges are arranged alternately and linearly.

As shown in FIG. 12, the charges stored in the CCD 27i (or 94i) are read out by the drive signals output from the drive circuit 119. For such readout operation, interlace scanning is performed, that is to say, as shown in FIG. 14, in the case of readout of the first field, the signals in the pixels in a pair of odd and even lines which are vertically adjacent to each other, such as the first and second lines, the third and fourth lines, . . . , are added and the result is output, and, in the case of readout of the second field, the signals in the pixels in a pair of even and odd lines which are vertically adjacent to each other, such as the second and third lines, the fourth and fifth lines, . . . , are added and the result is output.

Each combination of two pixels which are vertically adjacent to each other and two pixels which are horizontally adjacent to each other contains Ye, Mg, Cy and G. Therefore, if these color components are added, 2R+3G+2B is obtained, and the result is rendered as a luminance signal.

Addition of two vertically adjacent lines is performed in the CCD 27i (or 94i), and addition of two horizontally adjacent lines is performed by eliminating clock components from the output signals of the CCD 27i in a correlative double sampling (abbreviated as "CDS") circuit 120, passing the result through a low-pass filter (LPF) 121 and integrating the output of the LPF 121.

The signal passed through the LPF 121 is input to the AGC circuit 45 and the light-adjustment-signal generating circuit 46 in a manner similar to that used in the first embodiment. The output signal of the AGC circuit 45 is input to both a process circuit 122 and an AGC control section 63.

After processings such as color separation and $\gamma$ correction have been effected, a luminance signal Y and a line-sequential color-difference signals LC (R-Y and B-Y) are output.

The luminance signal Y is converted into a corresponding digital amount by an A/D converter 123 and the digital amount is stored in a Y frame memory 124a. The color difference signals LC, that is, the color difference signals R-Y and B-Y are sequentially (alternately) output every other line. After the color difference signals R-Y and B-Y have been stored in an A/D converter 125, the signal of the R-Y line is stored in an R-Y frame memory 124b, while the signal of the B-Y line is stored in a B-Y frame memory 124c.

The luminance signal of the Y frame memory 124a is sequentially read out in line-by-line fashion. However, since the R-Y and B-Y signals are alternately supplied every other line, the same R-Y and B-Y signals are read out for two lines for the purpose of simultaneous processing with respect to the luminance signal Y. Writing/reading of the frame memories 124a, 124b and 124c is controlled by a memory control section 126.

The signals read from the frame memories 124a, 124b and 124c are converted into analog signals in corresponding D/A converters 51a, 51b and 51c in a manner similar to that used in the first embodiment. The analog signals are then input to an NTSC encoder 52, converted into an NTSC composite video signal, and supplied from the output terminal to a color monitor.

As described previously in the first embodiment, the iris control circuit 43 responds to the output signal of the light-adjustment generating circuit 46 to drive the iris motor 42, thereby rotating the iris blade 41 to control the quantity of light going past the iris blade 41. Thus, the quantity of light incident upon the light guide 21 is controlled.

In other words, the quantity of illuminating light is controlled in accordance with the level of an image signal which is input to the light-adjustment-signal generating circuit 46 through the LPF 121.

In this fashion, if use conditions vary, for example, from imaging of an object at a short distance to that of an object at a relatively long distance, the quantity of illuminating light is controlled to automatically select a proper intensity of illumination so that an image which enables an operator to easily make correct diagnosis or inspection can be obtained.

The circuit constructions of the discriminating-signal generating circuit 61i, the discriminating circuit 62 and the AGC control section 63 may be similar to the circuit constructions of those used in the first embodiment.

In the second embodiment, since the interline-transfer type CCD is employed as built-in color-filter type imaging means, the charges stored can instantaneously be transferred to each adjacent light-tight transfer portion by the application of transfer pulses. Subsequently, when readout signals are applied to the transfer portions, the charges can be sequentially read out. In other words, even if the period in which illuminating light is shielded is not produced by means of the light source apparatus 113, exposure and readout of signal charges can be performed.

Where a line-transfer type CCD in which light receiving portions and transfer portions are formed in common is employed, the lamp 32 may be off for each transfer period.

The above line-transfer type CCD may be employed as the frame sequential-type imaging means used in the first embodiment. In this case, the width of each of the light shielding portions of the rotary color filter device 35 may be reduced to such an extent that the mixture of colors does not occur.

Figure 15:
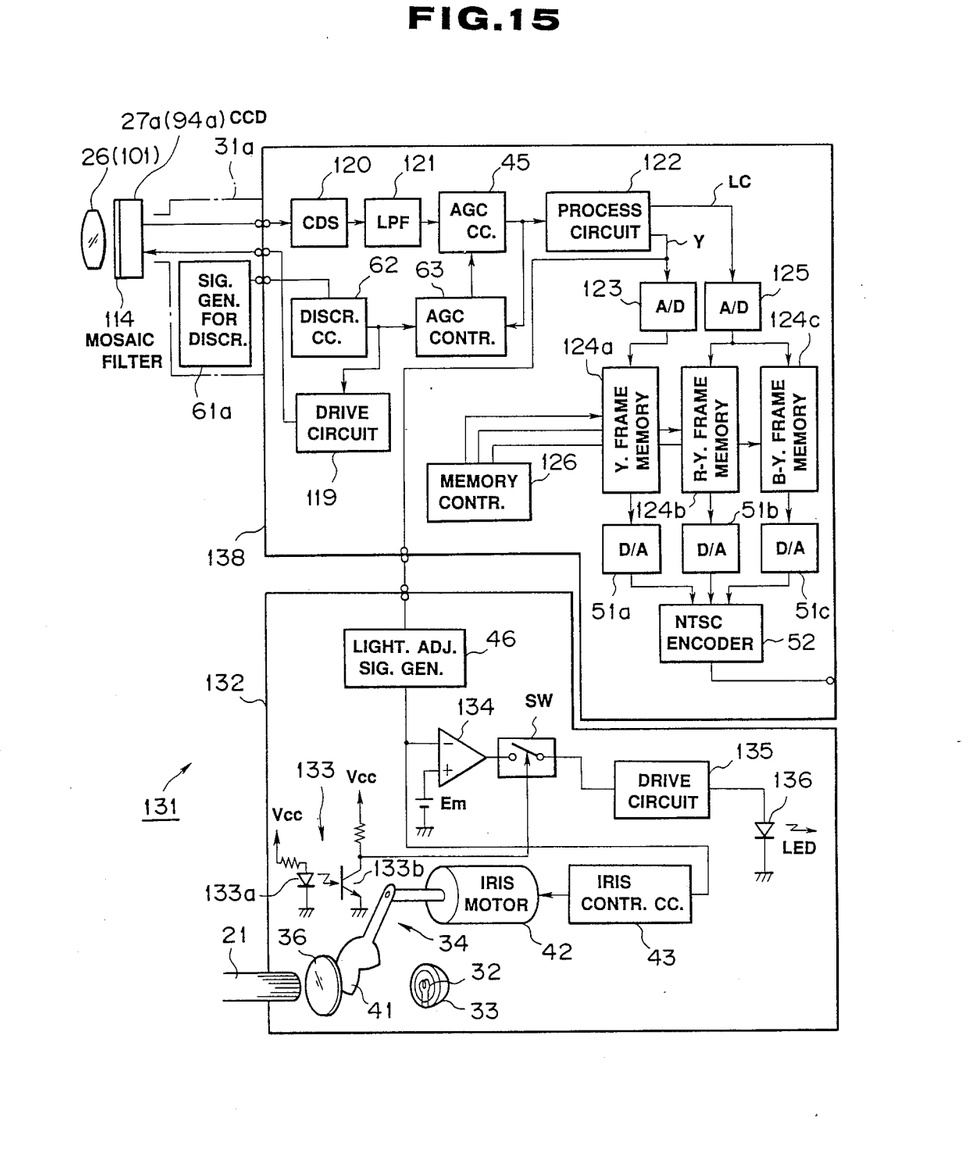
FIG. 15 is a block diagram showing the construction of the essential portion of a fourth embodiment of the present invention.

FIG. 15 shows an endoscope system 131 according to a fourth embodiment of the present invention.

The fourth embodiment is a modified version of the third embodiment of FIG. 12 in that, if the endoscope system 131 is not appropriately used, an operator is informed of that fact.

In a light source apparatus 132, a position sensor 133 is disposed for detecting the maximum intensity of illumination of the light source apparatus 132, that is, the fully open position of the iris blade 41. The output signal of the position sensor 133 is applied to the on-off control terminal of an analog switch SW. When the iris blade 41 is fully opened, the analog switch SW is switched on.

The output signal of the light-adjustment-signal generating circuit 46 is input to a comparator 134, in which the output signal is compared with a reference voltage Em corresponding to the minimum allowable luminance. If the voltage of the above output signal is not higher than the voltage Em, the output of the comparator 134 goes to a high level "H". The output of the comparator 134 is supplied through the analog switch SW to a drive circuit 135, and the output of the drive circuit 135 causes a warning LED 136 to be switched on. The above-described position sensor 133 may be constituted by, for example, a photointerrupter consisting of a light emitting diode 133a and a phototransistor 133b.

In the fourth embodiment, the light-adjustment-signal generating circuit 46 is arranged to receive the luminance signal Y output from the process circuit 122. In this case, a sampling pulse is input to the sample and hold circuit 46b (refer to FIG. 4) in the light-adjustment-signal generating circuit 46 in each field period for one frame of a color image. In this embodiment, the light-adjustment-signal generating circuit 46 is disposed in not the signal processing apparatus 138 but the light source apparatus 132.

In the fourth embodiment, even in the fully open state of the iris blade 41, if the average level of the luminance signal Y is smaller than the voltage Em corresponding to the minimum allowable level, the LED 136 lights. Accordingly, the operator can be informed that the illumination in the present use conditions is darker than that in proper use conditions. In this case, the operator may move the electronic endoscope or the fiber scope toward a portion to be observed.

In the fourth embodiment, since warning is given if any deviation from the proper use conditions is detected, the operator can immediately modify the present use conditions in accordance with use conditions which enable appropriate observation. This means that imaging under use conditions suitable for diagnosis is always enabled. Accordingly, since it is possible to obtain a good image with a high S/N ratio, the above-described embodiment is well suited for use with diagnosis.

It is to be noted that, in the fourth embodiment, the LED 136 is caused to light for the purpose of warning, but, instead, a buzzer may be used or a warning sign may be displayed on the color monitor.

Figure 16:
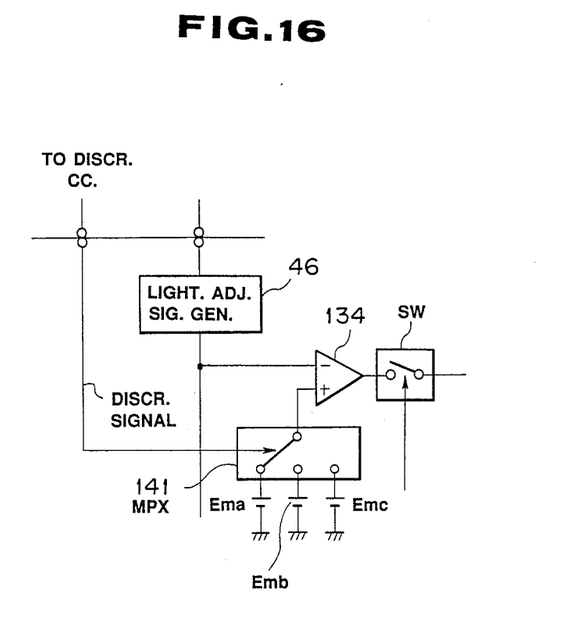
FIG. 16 is a block diagram showing the essential portion of a modified example of the fourth embodiment.

As shown in FIG. 16, a suitable voltage may be selected from among the minimum allowable voltages Ema, Emb and Emc by means of the multiplexer 141 in accordance with the output signal of the discriminating circuit 62, thereby making a decision as to each imaging means.

In each of the above-described embodiments, each of the maximum gain and the minimum gain is selectively set. However, for example, either the maximum gain or the minimum gain may be varied to set the gain variation region.

In each of the above-described embodiments, the gain variation region is automatically set in accordance with the number of pixels of each of the CCDs which constitute a plurality of electronic endoscopes. The gain variation region may be manually set.

In each of the above-described embodiments, a suitable gain variation region is selected from among a plurality of gain variation regions in accordance with each of the electronic endoscopes. However, the present invention is applicable to an arrangement, using a single electronic endoscope, in which a suitable one is selected from among the gain variation regions in accordance with, for example, the number of pixels of the solid state imaging device of the electronic endoscope employed.

It will be appreciated that, if portions of the above-described embodiments are combined with one another, different embodiments can be provided.

What is claimed is:

1. An electronic-type endoscope system comprising:
   (a) an electronic endoscope including
      an elongated inserting section,
      light emitting means for emitting illuminating light from one end of said inserting section, and
      imaging means constituted by an objective optical system attached to said one end of said inserting section and a solid state imaging device for photoelectrically converting an optical image obtained by said objective optical system;
   (b) signal processing means for converting an image signal output from said imaging means into a standard image signal;
   (c) monitor means for providing a display of said standard image signal output from said signal processing means;
   (d) automatic gain control means constituting said signal processing means and arranged to automatically output said standard image signal whose level is automatically adjusted to a proper level in accordance with a level of said image signal; and
   (e) gain variation region setting means for setting a gain variation region of said automotive gain control means based upon a control signal representing characteristics of an apparatus to be connected.

2. An endoscope system according to claim 1, wherein said apparatus to be connected is said electronic endoscope.

3. An endoscope system according to claim 1, wherein said electronic endoscope is an electronic scope in which said solid state imaging device is disposed in a focal plane of said objective optical system.

4. An endoscope system according to claim 1, wherein said electronic endoscope is a scope of a type to which a television camera is externally attached and which is constituted by an optical endoscope which has an image guide for transferring an optical image obtained by said objective optical system and a television camera which is detachably attached to an eyepiece portion of said optical endoscope for focusing said optical image transferred over said image guide on said solid state imaging device by means of a focusing optical system.

5. An endoscope system according to claim 3 or 4, wherein said solid state imaging device has an imaging surface at a front side of which a color filter for effecting color separation is disposed.

6. An endoscope system according to claim 3 or 4, wherein said solid state imaging device has an imaging surface at a front side of which no color filter for effecting color separation is disposed.

7. An endoscope system according to any one of claims 1, 3, or 4, wherein said light emitting means is a light guide which is arranged to receive light at an entrance end surface, transfer said light therethrough, and emit said light through an exit end surface.

8. An endoscope system according to claim 7 further comprising a light source apparatus for supplying light to the entrance end surface of said light guide.

9. An endoscope system according to claim 8, wherein said light source apparatus has light adjustment means for adjusting a quantity of light inCident upon the entrance end surface of said light guide in accordance with the level of said image signal output from said solid state imaging device.

10. An endoscope system according to claim 9, wherein said light adjustment means is constituted by an iris and an iris driving motor for changing an aperture of said iris.

11. An endoscope system according to any one of claims 1, 3, or 4, wherein said gain variation region control means outputs a control signal which serves to determine at least one of a maximum gain and a minimum gain of said automatic gain control means.

12. An endoscope system according to any one of claims 1, 3, or 4 further comprising comparing means for determining whether or not an average level of said image signal of said imaging means is lower than a minimum allowable level when a quantity of illuminating light emitted from said light emitting means is at a maximum.

13. An endoscope system according to claim 12, wherein said comparing means causes a warning means to operate when said comparing means has determined that said average level is lower than said minimum allowable level.

14. An electronic-type endoscope comprising:
a first electronic endoscope including a first objective optical system and a first light emitting means both of which are disposed at a front end portion of a first elongated inserting section as well as a first imaging means constituted by a first solid state imaging device for photoelectrically converting an optical image obtained by said first objective optical system;
a second electronic endoscope including a second objective optical system and a second light emitting means both of which are disposed at a front end portion of a second elongated inserting section as well as a second imaging means constituted by a second solid state imaging device for photoelectrically converting an optical image obtained by said second objective optical system;
signal processing means for converting image signals output form said first and second imaging means into standard image signals;
monitor means for providing a display of said standard image signals output from said signal processing means;
automatic gain control means constituting said signal processing means and arranged to automatically output image signals whose levels are automatically adjusted to proper levels in accordance with levels of said respective image signals; and
gain variation region setting means for outputting a plurality of control signals to set a gain variation region of said automatic gain control means to a plurality of gain regions.

15. An endoscope system according to claim 14, wherein numbers of pixels of said first and second electronic endoscopes differ from each other.

16. An endoscope system according to claim 14 or 15, wherein said gain variation region varying means is capable of selectively outputting a plurality of control signals which serve to define at least one of a maximum gain and a minimum gain of said automatic gain control means in correspondence with said first and second electronic endoscopes.

17. An endoscope system according to claim 16, wherein each of said first and second electronic endoscopes has a discriminating-signal generating means for generating a discriminating signal which serves to identify the imaging means of each of said first and second electronic endoscopes.

18. An endoscope system according to claim 17, wherein said signal processing means has a decoding means for decoding said discriminating signal.

19. An endoscope system according to claim 18, wherein said gain variation region setting means constitutes an automatic selecting means for automatically selecting a desired control signal from among said plurality of control signals in accordance with a decode signal output from said decoding means.

20. An endoscope system according to claim 14 or 15, wherein at least one of said first and second electronic endoscopes is an electronic endoscope in which a corresponding one of said first and second solid state imaging devices is disposed in a focal plane of a corresponding one of said first and second objective optical systems.

21. An endoscope system according to claim 14 or 15, wherein at least one of said first and second electronic endoscope is a scope of a type to which a television camera is externally attached and which is constituted by an optical endoscope which has an image guide for transferring an optical image obtained by the corresponding one of said first and second objective optical systems and a television camera which is detachably attached to an eyepiece portion of said optical endoscope for focusing said optical image transferred over said image guide on the corresponding one of said first and second solid state imaging devices by means of a focusing optical system.

22. An endoscope system according to claim 20, wherein at least one of said first and second solid state imaging devices has an imaging surface at a front side of which a color filter for effecting color separation is disposed.

23. An endoscope system according to claim 20, wherein at least one of said first and second solid state imaging devices has an imaging surface at a front side of which no color filter for effecting color separation is disposed.

* * * * *